(12) United States Patent
Mousa et al.

(10) Patent No.: US 7,736,636 B2
(45) Date of Patent: Jun. 15, 2010

(54) METHOD FOR TREATING OCCLUSIVE VASCULAR DISEASES & WOUND HEALING

(76) Inventors: Shaker Mousa, 5 Fox Glove Ct., Wynantskill, NY (US) 12198; Sarah Mousa, 5 Fox Glove Ct., Wynantskill, NY (US) 12198

( * ) Notice: Subject to any disclaimer, the term of this patent is extended or adjusted under 35 U.S.C. 154(b) by 1119 days.

(21) Appl. No.: 10/776,383

(22) Filed: Feb. 11, 2004

(65) Prior Publication Data

US 2005/0069518 A1 Mar. 31, 2005

(51) Int. Cl.
  *A61K 38/18* (2006.01)
  *A61K 31/785* (2006.01)
  *A61K 31/4439* (2006.01)
  *A61K 31/7076* (2006.01)
  *A61K 31/52* (2006.01)
  *A61K 31/21* (2006.01)

(52) U.S. Cl. .................. 424/78.3; 514/12; 514/263.4; 514/294; 514/356; 514/46; 514/509

(58) Field of Classification Search ............... 514/356, 514/353, 263.4; 424/78.3
  See application file for complete search history.

(56) References Cited

U.S. PATENT DOCUMENTS

| | | | | |
|---|---|---|---|---|
| 4,067,876 A | * | 1/1978 | Ferruti et al. | 525/326.7 |
| 4,169,923 A | * | 10/1979 | Ferruti et al. | 525/279 |
| 4,329,338 A | * | 5/1982 | Szego et al. | 514/27 |
| 4,415,570 A | * | 11/1983 | Enomoto et al. | 514/236.2 |
| 5,219,564 A | * | 6/1993 | Zalipsky et al. | 424/78.17 |
| 6,015,821 A | * | 1/2000 | Horrobin et al. | 514/355 |
| 6,495,161 B1 | * | 12/2002 | Soon-Shiong et al. | 424/451 |
| 6,630,491 B1 | * | 10/2003 | Zoltewicz et al. | 514/334 |
| 6,821,524 B2 | * | 11/2004 | Marini | 424/401 |
| 2002/0128298 A1 | * | 9/2002 | Jaccobson et al. | 514/356 |

FOREIGN PATENT DOCUMENTS

| | | | |
|---|---|---|---|
| BE | 716361 A | * | 12/1968 |
| FR | 7037 M | * | 7/1969 |

OTHER PUBLICATIONS

Grover et al., Pediatr Res., abstract, Dec. 2002; 52(6):907-12.*
"Controlled Release of Oral Drugs from Cross-Linked Polyvinyl Alcohol Microspheres", Thanoo et al., J. Pharm. Pharmcol., 1993, 45:16-20.*
"Vascular Endothelail Growth Factor Stimulates Differential Pathways in In Vivo Microcirculation", Aramoto et al., American Journal of Physiology, abstract, 2004, vol. 56, No. 4, pp. H1590-H1598.*

* cited by examiner

*Primary Examiner*—Brian-Yong S Kwon
(74) *Attorney, Agent, or Firm*—Schmeiser Olsen & Watts

(57) ABSTRACT

Disclosed are methods of treating subjects having conditions related to angiogenesis including administering an effective amount of a polymeric form of Nicotine, nicotinic acid analogs thereof, their combination with or without other pro-angiogenesis factors, vasodilator, or other therapeutic modalities to promote angiogenesis in the subject. This is composition and combination thereof is applicable to improving wound healing, erectile dysfunction, improving collateral or blood supply in patients with myocardial infarction, stroke, peripheral artery diseases, and other vascular disorders as disclosed.

16 Claims, 4 Drawing Sheets

Nicotinic acid or niacin is 3-pyridinecarboxylic acid.

M = metals - sodium, potassium, etc. or ammonium salt

Esters, where R = alkyl, aryl, polymer and substituted variants thereof.

Esters are known to undergo hydrolysis *in vivo* to give the carboxylate.

Amides, $R_1$ or $R_2$ = hydrogen, alkyl, aryl, polymer

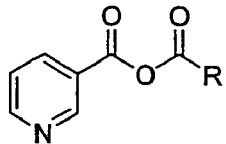 Anhydrides, where R = alkyl, aryl, polymer and substituted variants thereof.

Anhydrides are typically very reactive in water and hydrolyze to the carboxylate rapidly.

Figure 1E

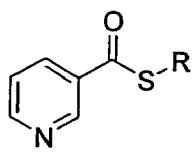 Thioesters, where R = alkyl, aryl, polymer

In general, thioesters are less susceptible towards hydrolysis than esters.

Figure 1F

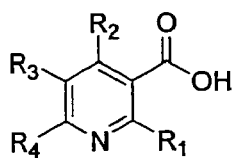 Ring derivatives, where R1 – R4 = alkyl, aryl, polymer, halides, ethers,

Figure 1G

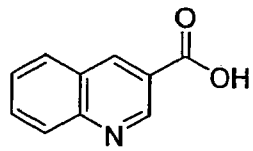
3-quinolinecarboxylic acid

Figure 1H

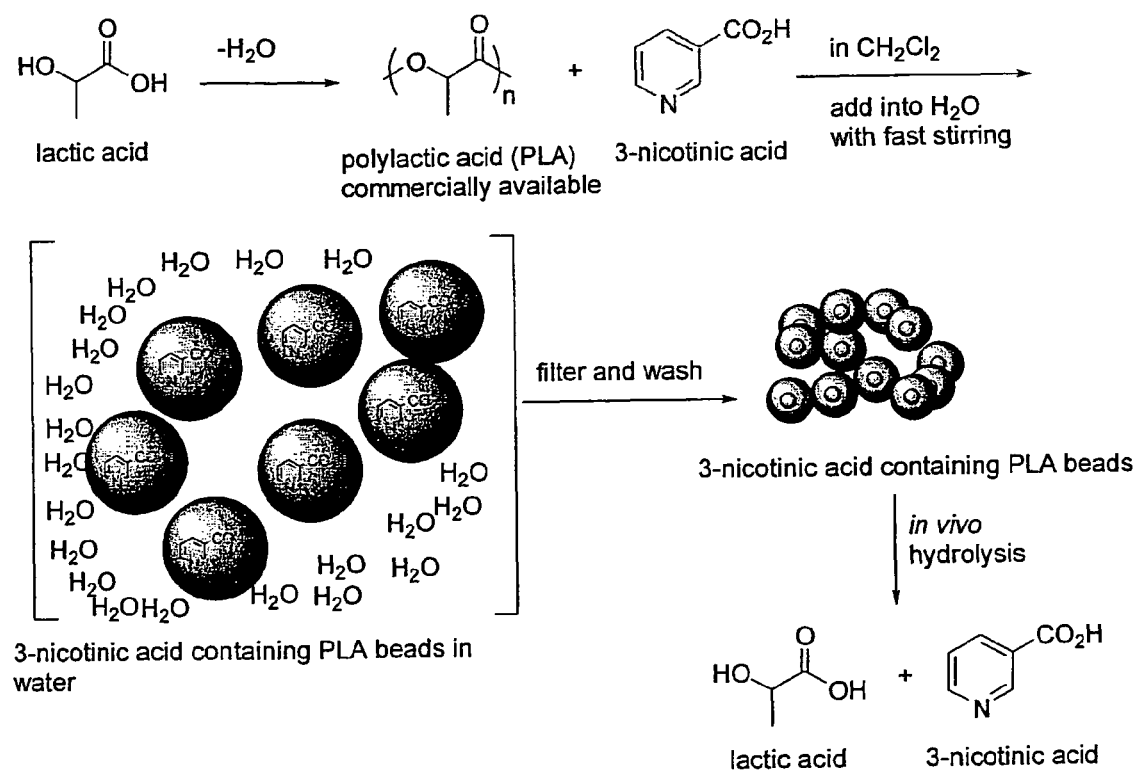
(Figure 4)

METHOD FOR TREATING OCCLUSIVE VASCULAR DISEASES & WOUND HEALING

FIELD OF THE INVENTION

Compositions and methods for treatment of wound healing, occlusive peripheral vascular, carotid and coronary disease are disclosed. The compositions and methods allow treatment of diseases associated with occlusion of coronary vessels, for example, by promoting growth of new blood vessels, i.e., angiogenesis and/or by recruitment of collaterals. The methods involve the administration of polymeric forms of Nicotinic acid derivatives or nicotine alone or in combination with other pro-angiogenesis agents and/or vasodilators over a period of several days. In particular, this invention is applicable to improving wound healing, collateral coronary, peripheral artery, and carotid circulation in patients suffering from impaired wound healing, impotence, erectile dysfunction, myocardial infarction, peripheral artery diseases, other vascular occlusive disorders such as sickle cell disease, and stroke.

BACKGROUND OF THE INVENTION

It is estimated that five million people are afflicted with chronic stable angina in the United States. Each year 200,000 people under the age of 65 die with what is termed "premature ischemic heart disease." Despite medical therapy, many go on to suffer myocardial infarction and debilitating symptoms prompting the need for revascularization with either percutaneous transluminal coronary angioplasty or coronary artery bypass surgery. Medical researchers have postulated that one way of relieving myocardial ischemia would be to enhance coronary collateral circulation.

Fujita et. al. (Fujita et al., Am. Heart Journal., 122:453 (1991), Fujita et al., Int. J. Cardiol., 40:51 (1993) demonstrated that heparin in combination with short-term exercise training improved exercise tolerance as measured by dynamic exercise testing. The researchers, believing this effect was mediated through increased collateral vascular development, examined the effects of heparin in combination with a brief concomitant exercise training protocol on coronary collateral flow. Thallium-201 myocardial perfusion images obtained in association with the same workload both before and late after combined heparin exercise treatment, which indicated that coronary collateral circulation was enhanced. Such dramatic changes over a short term do not occur naturally, and suggest that angiogenesis has taken place.

Correlations have now been made between the anatomic appearance of coronary collateral vessels ("collaterals") visualized at the time of intracoronary thrombolitic therapy during the acute phase of myocardial infarction and the creatine kinase time-activity curve, infarct size, and aneurysm formation. These studies demonstrate a protective role of collaterals in hearts with coronary obstructive disease, showing smaller infarcts, less aneurysm formation, and improved ventricular function compared with patients in whom collaterals were not visualized.

When the cardiac myocyte is rendered ischemic, collaterals develop actively by growth with DNA replication and mitosis of endothelial and smooth muscle cells. One hypothesis suggests that heparin-binding growth factors are present in the heart, or that biological activity is quiescent under normal physiological conditions. Once ischemia develops, these factors are activated and become available for receptor occupation, which may initiate angiogenesis after exposure to exogenous heparin. Unfortunately, the "natural" process by which angiogenesis occurs is inadequate to reverse the ischemia in almost all patients with coronary artery disease.

During ischemia, adenosine is released through the breakdown of ATP. Adenosine participates in many cardio-protective biological events. Adenosine has a role in hemodynamic changes such as bradycardia and vasodilation, and adenosine has been suggested to have a role in such unrelated phenomena as preconditioning and possibly the reduction in reperfusion injury (Ely and Beme, Circulation, 85: 893 (1992).

Intrinsic adenosine may facilitate the coronary flow response to increased myocardial oxygen demands and so modulate the coronary flow reserve. Ethier et. al. (Ethier et al., Am. J. Physiol., H131 (1993) demonstrated that the addition of physiological concentrations of adenosine to human umbilical vein endothelial cell cultures stimulates proliferation, possibly via a surface receptor. They suggested that adenosine may be a factor for human endothelial cell growth and possibly angiogenesis. Angiogenesis appears to be protective for patients with CAD, but the rate at which blood vessels grow naturally is inadequate to reverse the disease. Thus, strategies to enhance and accelerate the body's natural angiogenesis potential should be beneficial in patients with CAD.

There remains a need for an effective therapy for promotion of coronary angiogenesis with minimum side effects. Such a therapy would be particularly useful for patients who have myocardial infarctions and could be used prophylactically in patients who have poor coronary circulation, which places them at high risk of ischemia and myocardial infarctions.

Nicotine stimulates new blood vessel growth: Most forms of smoking cessation treatment involve the use of nicotine without tobacco. Thus, the effects of such doses of nicotine on the body are crucial. However, according to new research published in the July issue of (Nature Medicine, Vol. 7, 833, 2001), the bad news for those using these products to stop smoking is that nicotine without tobacco can cause angiogenesis, which in turn aids the growth of atherosclerotic plaques and tumors.

SUMMARY OF THE INVENTION

The invention is based, in part, on the discovery that nicotine, nicotinic acid analogs, and their polymeric forms have pro-angiogenesis properties. Accordingly, these Nicotine, nicotinic acid analogs, and polymeric forms (i.e., pro-angiogenesis agents) can be used to treat a variety of deficient angiogenesis-mediated disorders.

Accordingly, in one aspect the invention features methods for treating a condition amenable to treatment by promoting angiogenesis by administering to a subject in need thereof an amount of a polymeric form of Nicotine, nicotinic acid analogs, or an analog thereof, effective for promoting angiogenesis. Examples of such conditions amenable to treatment by promoting angiogenesis are provided herein and can include occlusive vascular disease, sickle cell diseases, coronary disease, erectile dysfunction, myocardial infarction, ischemia, stroke, peripheral artery vascular disorders, and wounds.

Over 150 million men worldwide suffer from erectable dysfunction and only a small percentage is being treated for it. Although a number of diseases such as diabetes can be the cause, in most cases the underlying problem can't be identified. Viagra was the first oral drug to be approved by the U.S. Food and Drug Administration for erectility dysfunction. Since its approval, over 17 million men have received Viagra worldwide. Other manufacturers are rushing products through clinical trials to compete with Viagra. Viagra, Levitra and Cialis all work to reduce the effects of an enzyme called PDE5. Reducing the activity of the PDE5 enzyme means more blood can flow to the penis and less leaves. A combined use of nicotine, nicotinic acid, derivatives, or polymer conjugate topically or systemically with hormonally inactive analogs that sustain potent pro-angiogenesis effects would be of value in enhancing the effects of other standard therapies such as listed above, vasodilators, and others.

Examples of Nicotine, nicotinic acid analogs or conjugated to polyvinyl alcohol, acrylic acid ethylene co-polymer, poly-Lactic acid, or polyethylene glycol on the carboxylic acid terminal are also provided herein. The conjugation is via covalent or non-covalent bonds depending on the polymer used.

In one embodiment the Nicotine, nicotinic acid analogs, or polymeric forms thereof are administered by parenteral, oral, rectal, or topical means, or combinations thereof. Parenteral modes of administration include, for example, subcutaneous, intraperitoneal, intramuscular, or intravenous modes, such as by catheter. Topical modes of administration can include, for example, a band-aid.

In another embodiment, Nicotine, nicotinic acid analogs, or polymeric forms thereof can be encapsulated or incorporated in a microparticle, liposome, or polymer. The polymer can include, for example, polyglycolide, polylactide, or co-polymers thereof. The liposome or microparticle has a size of about less than 200 nanometers, and can be administered via one or more parenteral routes, or another mode of administration. In another embodiment the liposome or microparticle can be lodged in capillary beds surrounding ischemic tissue, or applied to the inside of a blood vessel via a catheter.

Nicotine, nicotinic acid analogs, or polymeric forms thereof according to the invention can also be co-administered with one or more biologically active substances that can include, for example, growth factors, vasodilators, anti-coagulants, anti-virals, anti-bacterials, anti-inflammatories, immuno-suppressants, analgesics, vascularizing agents, or cell adhesion molecules, or combinations thereof. In one embodiment, the Nicotine, nicotinic acid analogs or polymeric form is administered as a bolus injection prior to or post-administering one or more biologically active substance.

Nicotine, nicotinic acid analogs based on this invention provides methods for treating vascular occlusive diseases including venous and arterial disorders ranging from venous thromboembolic disorders (deep vein thrombosis, sickle cell diseases, and pulmonary embolism), and arterial thromboembolic disorders (coronary artery diseases, cerebrovascular disorders, and peripheral artery diseases). Nicotine, nicotinic acid analogs can be used alone or in conjunction with other standard therapies for vascular disorders.

Growth factors can include, for example, basic fibroblast growth factor, vascular endothelial growth factor, epithelial growth factor, nerve growth factor, platelet-derived growth factor, and vascular permeability factor. Vasodilators can include, for example, adenosine, adenosine derivatives, or combinations thereof. Anticoagulants include, but are not limited to, heparin, heparin derivatives, anti-factor Xa, anti-thrombin, aspirin, clopidgrel, or combinations thereof.

In another aspect of the invention, methods are provided for promoting angiogenesis along or around a medical device by coating the device with a Nicotine, nicotinic acid analogs, or polymeric form thereof according to the invention prior to inserting the device into a patient. The coating step can further include coating the device with one or more biologically active substance, such as, but not limited to, a growth factor, a vasodilator, an anti-coagulant, or combinations thereof. Examples of medical devices that can be coated with Nicotine, nicotinic acid analogs or polymeric forms according to the invention include stents, catheters, cannulas or electrodes.

In yet a further aspect, the invention provides compositions (i.e., pro-angiogenesis agents) that include Nicotine, nicotinic acid, and analogs conjugated to a polymer. The conjugation can be through a covalent or non-covalent bond, depending on the polymer. A covalent bond can occur through an ester or anhydride linkage, for example. In one embodiment, the polymer can include, but is not limited to, polyvinyl alcohol, acrylic acid ethylene co-polymer, polylactic acid, or polyethylene glycols.

In another aspect, the invention provides for pharmaceutical formulations including the pro-angiogenesis agents according to the present invention in a pharmaceutically acceptable carrier. In one embodiment, the pharmaceutical formulations can also include one or more pharmaceutically acceptable excipients.

The pharmaceutical formulations according to the present invention can be encapsulated or incorporated in a liposome, microparticle, or polymer. The liposome or microparticle has a size of less than about 200 nanometers. Any of the pharmaceutical formulations according to the present invention can be administered via parenteral, oral, rectal, or topical means, or combinations thereof. In another embodiment, the pharmaceutical formulations can be co-administered to a subject in need thereof with one or more biologically active substances including, but not limited to, growth factors, vasodilators, anti-coagulants, or combinations thereof.

The details of one or more embodiments of the invention have been set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural references unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference in their entirety.

Compositions and methods for treatment of occlusive peripheral vascular disease and coronary diseases, in particular, the occlusion of coronary vessels, and disorders associated with the occlusion of the peripheral vasculature and/or coronary blood vessels are disclosed. Also disclosed are compositions and methods for promoting angiogenesis and/or recruiting collateral blood vessels in a patient in need thereof. The compositions include an effective amount of polymeric forms of nicotinic acid and nicotine and an effective amount of an adenosine and/or nitric oxide donor. The compositions can be in the form of a sterile, injectable, pharmaceutical formulation that includes an angiogenically effective amount of nicotinic acid and nicotine-like substance and adenosine derivatives in a physiologically and pharmaceutically acceptable carrier, optionally with one or more excipients.

We have made the startling observation that either nicotine or nicotinic acid (Vitamin B3) and derivatives have potent pro-angiogenic properties. The angiogenic effects of nicotine but not nicotinic acid are mediated in part by an endothelial nicotinergic receptor, the vitronectin receptors and the release of endothelial basic fibroblast growth factor (FGF2). The angiogenic effects of nicotinic acid and derivatives are mediated in part by the release of endothelial FGF2.

The methods involve the co-administration of an effective amount of nicotinic acid and nicotine-like substance or polymeric forms and an effective amount of an adenosine and/or NO donor in low, daily dosages for a week or more. One or both components can be delivered locally via catheter. Nicotinic acid or nicotine, and derivatives in vivo can be delivered to capillary beds surrounding ischemic tissue by incorporation of the compounds in an appropriately sized liposome or microparticle. Nicotinic acid or nicotine, polymeric forms and derivatives can be targeted to ischemic tissue by covalent linkage with a suitable antibody.

The method may be used as a treatment to restore cardiac function after a myocardial infarction. The method may also be used to improve blood flow in patients with coronary artery disease suffering from myocardial ischemia or inadequate blood flow to areas other than the heart, for example, occlusive peripheral vascular disease (also known as peripheral arterial occlusive disease), where decreased blood flow is a problem.

BRIEF DESCRIPTION OF THE DRAWINGS

Nicotine or Nicotinic acid promoted new blood vessel generation in the CAM model (Table 1). Nicotine resulted in comparable pro-angiogenesis effect to that shown with FGF2 (Table 2).

FIGS. 1A-H: Examples of Nicotinic acid derivatives. The compositions of the present invention may include the nicotinic acid derivatives in FIGS. 1A-H alone or as conjugated with different polymers as shown, for example, in FIGS. 2-4.

FIG. 4: Polymer Compositions of Nicotine, nicotinic acid analogs—Entrapment in a Polylactic Acid Polymer. Polylactic acid polyester polymers (PLA) undergo hydrolysis in vivo to the lactic acid monomer and this has been exploited as a vehicle for drug delivery systems in humans. Unlike the prior two covalent methods where the Nicotine, nicotinic acid analogs peptide is linked by a chemical bond to the polymer, this would be a non-covalent method that would encapsulate the Nicotine, nicotinic acid analogs into PLA polymer beads. This reaction will lead to the formation of Nicotine, nicotinic acid analogs containing PLA beads in water. Filter and washing will result in the formation of Nicotine, nicotinic acid analogs containing PLA beads, which upon in vivo hydrolysis will lead to the generation of controlled levels of Nicotine, nicotinic acid analogs plus lactic acid.

DETAILED DESCRIPTION OF THE INVENTION

Figure 1A:
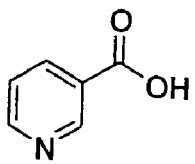
Figure 1B:
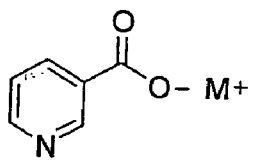
Figure 1C:
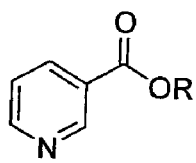
Figure 1D:
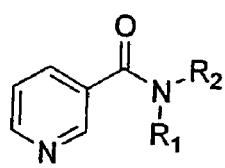
Figure 2:
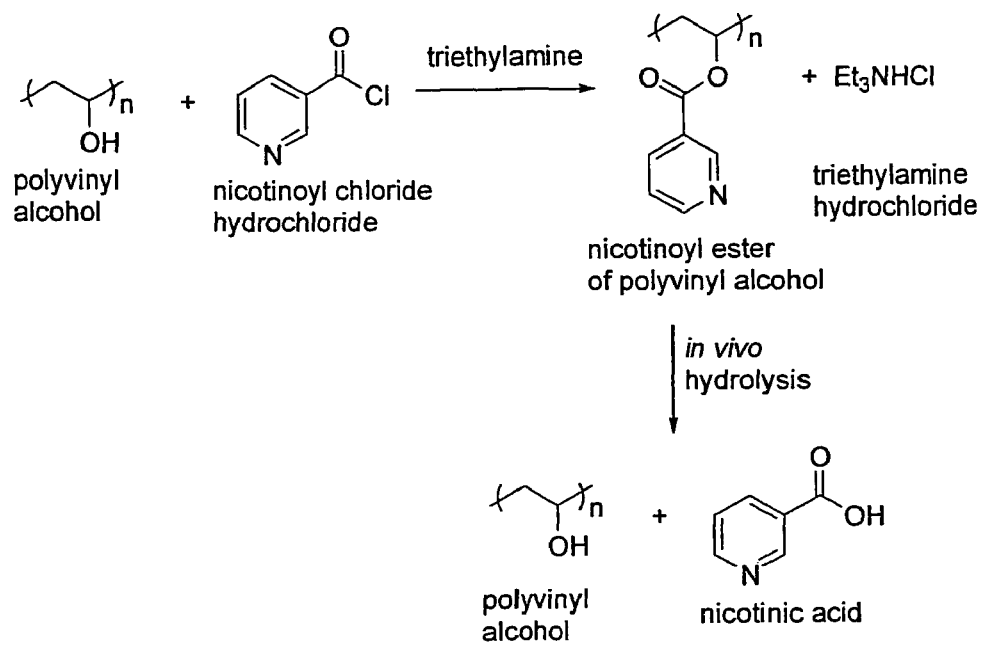
FIG. 2: Polymer Compositions of Nicotine, nicotinic acid analogs and Analogs—Polymer Conjugation through an Ester Linkage Using Polyvinyl Alcohol. In this preparation commercially available polyvinyl alcohol (or related co-polymers) can be esterified by treatment with the acid chloride form of the Nicotine or nicotinic acid derivatives. The hydrochloride salt is neutralized by the addition of triethylamine to afford triethylamine hydrochloride which can be washed away with water upon precipitation of the Nicotine, nicotinic acid analogs peptide ester polymer form for different analogs. The ester linkage to the polymer may undergo hydrolysis in vivo to release the active pro-angiogenesis nicotinic acid or nicotine.

The features and other details of the invention will now be more particularly described with references to the accompanying drawings, and as pointed out by the claims. For convenience, certain terms used in the specification, examples and claims are collected here. Unless otherwise defined, all technical and scientific terms used herein have the same meaning as commonly understood by one of ordinary skill in the art to which this invention pertains.

As used herein, the term "angiogenic agent" includes any compound or substance that promotes or encourages angiogenesis, whether alone or in combination with another substance. Examples include, but are not limited to Nicotine, nicotinic acid analogs, or polymeric analogs.

As used herein, the term "myocardial ischemia" is defined as an insufficient blood supply to the heart muscle caused by a decreased capacity of the heart vessels. As used herein, the term "coronary disease" is defined as diseases/disorders of cardiac function due to an imbalance between myocardial function and the capacity of coronary vessels to supply sufficient blood flow for normal function. Specific coronary diseases/disorders associated with coronary disease which can be treated with the compositions and methods described herein include myocardial ischemia, angina pectoris, coronary aneurysm, coronary thrombosis, coronary vasospasm, coronary artery disease, coronary heart disease, coronary occlusion and coronary stenosis.

As used herein the term "occlusive peripheral vascular disease" (also known as peripheral arterial occlusive disorder) is a vascular disorder-involving blockage in the carotid or femoral arteries, including the iliac artery. Occlusive vascular diseases include but not limited to conditions in Sickle cell patients. Blockage in the femoral arteries causes pain and restricted movement. A specific disorder associated with occlusive peripheral vascular disease is diabetic foot, which affects diabetic patients, often resulting in amputation of the foot.

As used herein the terms "regeneration of blood vessels," "angiogenesis," "revascularization," and "increased collateral circulation" (or words to that effect) are considered as synonymous. The term "pharmaceutically acceptable" when referring to a natural or synthetic substance means that the substance has an acceptable toxic effect in view of its much greater beneficial effect, while the related the term, "physiologically acceptable," means the substance has relatively low toxicity. The term, "co-administered" means two or more drugs are given to a patient at approximately the same time or in close sequence so that their effects run approximately concurrently or substantially overlap. This term includes sequential as well as simultaneous drug administration.

"Pharmaceutically acceptable salts" refers to pharmaceutically acceptable salts of Nicotine, nicotinic acid analogs, polymeric forms, and derivatives, which salts are derived from a variety of organic and inorganic counter ions well known in the art and include, by way of example only, sodium, potassium, calcium, magnesium, ammonium, tetraalkyl ammonium, and the like; and when the molecule contains a basic functionality, salts of organic or inorganic acids, such as hydrochloride, hydro-bromide, tartrate, mesylate, acetate, maleate, oxalate and the like can be used as the pharmaceutically acceptable salt.

"Subject" includes living organisms such as humans, monkeys, cows, sheep, horses, pigs, cattle, goats, dogs, cats, mice, rats, cultured cells, and transgenic species thereof. In a preferred embodiment, the subject is a human. Administration of the compositions of the present invention to a subject to be treated can be carried out using known procedures, at dosages and for periods of time effective to treat the condition in the subject. An effective amount of the therapeutic compound necessary to achieve a therapeutic effect may vary according to factors such as the age, sex, and weight of the subject, and the ability of the therapeutic compound to treat the foreign agents in the subject. Dosage regimens can be adjusted to provide the optimum therapeutic response. For example, several divided doses may be administered daily or the dose may be proportionally reduced as indicated by the exigencies of the therapeutic situation.

"Administering" includes routes of administration which allow the compositions of the invention to perform their intended function, e.g., promoting angiogenesis. A variety of routes of administration are possible including, but not necessarily limited to parenteral (e.g., intravenous, intra-arterial, intramuscular, subcutaneous injection), oral (e.g., dietary), topical, nasal, rectal, or via slow releasing micro-carriers depending on the disease or condition to be treated. Oral, parenteral and intravenous administration is preferred modes of administration. Formulation of the compound to be administered will vary according to the route of administration selected (e.g., solution, emulsion, gels, aerosols, capsule). An appropriate composition comprising the compound to be administered can be prepared in a physiologically acceptable vehicle or carrier and optional adjuvant and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See generally, *Remington's Pharmaceutical Science,* 16th Edition, Mack, Ed. (1980).

"Effective amount" includes those amounts of pro-angiogenic compounds which allow it to perform its intended function, e.g., promoting angiogenesis in angiogenesis-related disorders as described herein. The effective amount will depend upon a number of factors, including biological activity, age, body weight, sex, general health, severity of the condition to be treated, as well as appropriate pharmacokinetic properties. For example, dosages of the active substance may be from about 0.01 mg/kg/day to about 500 mg/kg/day, advantageously from about 0.1 mg/kg/day to about 100 mg/kg/day. A therapeutically effective amount of the active substance can be administered by an appropriate route in a single dose or multiple doses. Further, the dosages of the active substance can be proportionally increased or decreased as indicated by the exigencies of the therapeutic or prophylactic situation.

"Pharmaceutically acceptable carrier" includes any and all solvents, dispersion media, coatings, antibacterial and antifungal agents, isotonic and absorption delaying agents, and the like which are compatible with the activity of the compound and are physiologically acceptable to the subject. An example of a pharmaceutically acceptable carrier is buffered normal saline (0.15M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

"Additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, e.g., in *Remington's Pharmaceutical Sciences.*

Compositions:

Disclosed herein are pro-angiogenic agents comprising of Nicotine, nicotinic acid analogs thereof, and polymer conjugates. The disclosed compositions can be used for promoting angiogenesis to treat disorders wherein angiogenesis is beneficial. As used herein, the term "angiogenic agent" includes any compound or substance that promotes or encourages angiogenesis, whether alone or in combination with another substance. Examples of Nicotine, nicotinic acid analogs include, but are not limited to compositions shown in FIGS. 3-5.

Polymer conjugations are used to improve drug delivery. While many old and new therapeutics are well-tolerated, many compounds need advanced drug discovery technologies to decrease toxicity, increase circulatory time, or modify biodistribution. One strategy for improving drug viability is the utilization of water-soluble polymers. Various water-soluble polymers have been shown to modify biodistribution, improve the mode of cellular uptake, change the permeability through physiological barriers, and modify the rate of clearance through the body. To achieve either a targeting or sustained-release effect, water-soluble polymers have been synthesized that contain drug moieties as terminal groups, as part of the backbone, or as pendent groups on the polymer chain.

Figure 3:
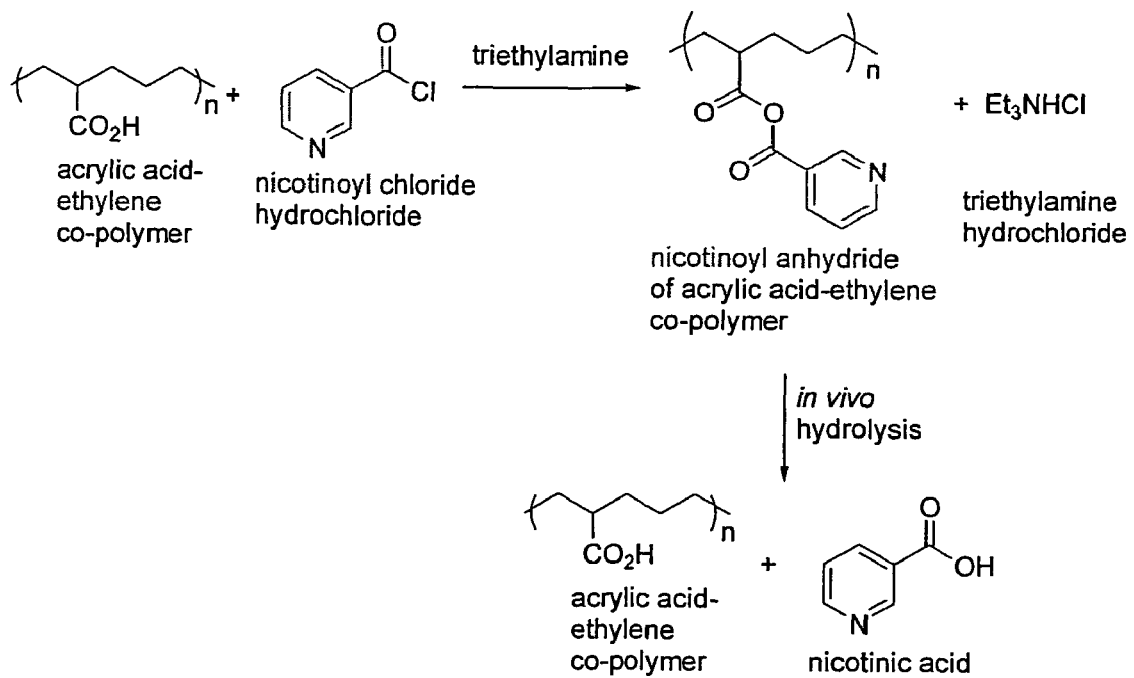
FIG. 3: Polymer Compositions of Nicotine, nicotinic acid analogs and Analogs—Polymer Conjugation through an Anhydride Linkage Using Acrylic Acid Ethylene Co-polymer. This is similar to the previous polymer covalent conjugation however this time it is through an anhydride linkage that is derived from reaction of an acrylic acid co-polymer. This anhydride linkage is also susceptible to hydrolysis in vivo to release Nicotine, nicotinic acid analogs. Neutralization of the hydrochloric acid is accomplished by treatment with triethylamine and subsequent washing of the precipitated polyanhydride polymer with water removes the triethylamine hydrochloride byproduct. This reaction will lead to the formation of Nicotine, nicotinic acid analogs acrylic acid co-polymer+triethylamine. Upon in vivo hydrolysis, the Nicotine, nicotinic acid analogs will be released over time that can be controlled plus acrylic acid ethylene Co-polymer.

Representative compositions of the present invention include Nicotine, nicotinic acid, analogs thereof conjugated to polymers. Conjugation with polymers can be either through covalent or non-covalent linkages. In preferred embodiments, the polymer conjugation can occur through an ester linkage or an anhydride linkage. An example of a polymer conjugation through an ester linkage using polyvinyl alcohol is shown in FIG. 3. In this preparation commercially available polyvinyl alcohol (or related co-polymers) can be esterified by treatment with the acid chloride of Nicotine, nicotinic acid analogs, including the acid chloride form. The hydrochloride salt is neutralized by the addition of triethylamine to afford triethylamine hydrochloride which can be washed away with water upon precipitation of the Nicotine, nicotinic acid analogs ester polymer form for different analogs. The ester linkage to the polymer may undergo hydrolysis in vivo to release the active pro-angiogenesis Nicotine, nicotinic acid analogs.

An example of a polymer conjugation through an anhydride linkage using acrylic acid ethylene co-polymer is shown in FIG. 4. This is similar to the previous polymer covalent conjugation, however, this time it is through an anhydride linkage that is derived from reaction of an acrylic acid co-polymer. This anhydride linkage is also susceptible to hydrolysis in vivo to release Nicotine, nicotinic acid analogs. Neutralization of the hydrochloric acid is accomplished by treatment with triethylamine and subsequent washing of the precipitated polyanhydride polymer with water removes the triethylamine hydrochloride byproduct. This reaction will lead to the formation of Nicotine, nicotinic acid analogs-acrylic acid co-polymer+triethylamine. Upon in vivo hydrolysis, the Nicotine, nicotinic acid analogs will be released over time that can be controlled plus acrylic acid ethylene Co-polymer.

Another representative polymer conjugation includes Nicotine, nicotinic acid analogs conjugated to polyethylene glycol (PEG). Attachment of PEG to various drugs, proteins and liposome has been shown to improve residence time and decrease toxicity. PEG can be coupled to active agents through the hydroxyl groups at the ends of the chains and via other chemical methods. PEG itself, however, is limited to two active agents per molecule. In a different approach, copolymers of PEG and amino acids were explored as novel biomaterials which would retain the biocompatibility properties of PEG, but which would have the added advantage of numerous attachment points per molecule and which could be synthetically designed to suit a variety of applications.

Another representative polymer conjugation includes Nicotine, nicotinic acid analogs in non-covalent conjugation with polymers. This is shown in detail in FIG. 5. A preferred non-covalent conjugation is entrapment of Nicotine, nicotinic acid analogs thereof in a polylactic acid polymer. Polylactic acid polyester polymers (PLA) undergo hydrolysis in vivo to the lactic acid monomer and this has been exploited as a vehicle for drug delivery systems in humans. Unlike the prior two covalent methods where the Nicotine, nicotinic acid analogs is linked by a chemical bond to the polymer, this would be a non-covalent method that would encapsulate the Nicotine, nicotinic acid analogs peptide or analogs into PLA polymer beads. This reaction will lead to the formation of Nicotine, nicotinic acid analogs containing PLA beads in water. Filter and washing will result in the formation of Nicotine, nicotinic acid analogs containing PLA beads, which upon in vivo hydrolysis hydrolysis will lead to the generation of controlled levels of Nicotine, nicotinic acid analogs plus lactic acid.

Furthermore, nanotechnology can be used for the creation of useful materials and structures sized at the nanometer scale. The main drawback with biologically active substances is fragility. Nano-scale materials can be combined with such biologically active substances to dramatically improve the durability of the substance, create localized high concentrations of the substance and reduce costs by minimizing losses. Therefore, additional polymeric conjugations include nano-particle formulations of Nicotine, nicotinic acid analogs thereof. In such an embodiment, nano-polymers and nano-particles can be used as a matrix for local delivery of Nicotine, nicotinic acid analogs. This will aid in time controlled delivery into the cellular and tissue target.

Compositions of the present invention include both nicotine, nicotinic acid analogs, and derivatives either alone or in covalent or non-covalent conjugation with polymers.

As provided above, methods for treatment of occlusive peripheral vascular disease and coronary diseases, in particular, the occlusion of coronary vessels, and disorders associated with the occlusion of the peripheral vasculature and/or coronary blood vessels are disclosed. Also disclosed are compositions and methods for promoting angiogenesis and/or recruiting collateral blood vessels in a patient in need thereof. The compositions include an effective amount of Nicotine, nicotinic acid or analogs, polymeric forms, and derivatives. The methods involve the co-administration of an effective amount of Nicotine, nicotinic acid analogs, polymeric forms, and derivatives in low, daily dosages for a week or more with other standard pro-angiogenesis growth factors, vasodilators, anticoagulants, thrombolytics or other vascular-related therapies.

The CAM assay has been used to validate angiogenic activity of a variety of growth factors and compounds believed to promote angiogenesis. A summary of the pro-angiogenesis effects of Nicotine, nicotinic acid, and analogs is listed in Table 1.

Example 1

Effect of Nicotine, nicotinic acid analogs on Angiogenesis: As seen in Table 1 below. Nicotine or nicotinic acid promotes new blood vessel branch formation in a CAM model that has been standardized previously for the assay of growth factors.

TABLE 1

Pro-angiogenesis effect of FGF2, Nicotine or Nicotinic acid in the CAM Model

| Treatment | Mean Number of Branch Points ± SD |
| --- | --- |
| Control | 76 ± 10 |
| FGF2 (1.0 µg) | 195 ± 22** |
| Nicotine (0.1 µg) | 192 ± 11** |
| Nicotinic acid (1.0 µg) | 155 ± 16* |
| Nicotinic acid polymer I (1.0 ug) | 188 + 14* |

Data represent average branch point ± SD, n = 8,
*$P < 0.01$,
**$P < 0.001$.
Nicotinic acid polymer conjugated through an ester linkage with polyvinyl alcohol.

Example 2

Nicotine, Nicotinic Acid and FGF2

TABLE 2

Effect of Nicotine on Release of FGF2 From Endothelial Cells

| Cell Treatment | Average number of branch Points ± SD |
| --- | --- |
| Control | 86 ± 14 |
| FGF2 (1.0 ug) | 195 ± 22** |
| Nicotine (0.1 ug) | 192 ± 11** |
| FGF2 (0.5 ug) | 115 ± 08* |
| Nicotine (0.05 ug) | 145 ± 10* |
| FGF2 (0.5 ug) + Nicotine (0.05 ug) | 225 ± 15** |

Data represent mean ± SD, n = 16,
*$P < 0.05$,
**$P < 0.001$ comparing nicotine-treated samples with control samples by ANOVA;
Similar data were shown with Nicotinic acid or its polymeric forms.

Example 3

In vitro human epithelial and fibroblast wound healing: The in vitro 2-dimensional wound healing method is as described in Mohamed S, Nadijcka D, Hanson, V. Wound healing properties of cimetidine in vitro. Drug Intell Clin Pharm 20: 973-975; 1986, incorporated herein by reference in its entirety. Additionally, a 3-dimensional wound healing method already established in our Laboratory will be utilized in this study (see below). Data show potent stimulation of wound healing by Nicotine (FIG. 7), nicotinic acid analogs.

In Vitro 3D Wound Healing Assay of Human Dermal Fibroblast Cells:
  Step 1: Prepare Contracted Collagen Gels:
  1) Coat 24-well plate with 350 ul 2% BSA at RT for 2 hr,
  2) 80% confluent NHDF (normal human dermal fibroblast cells, Passage 5-9) are trypsinized and neutralized with growth medium, centrifuge and wash once with PBS
  3) Prepare collagen-cell mixture, mix gently and always on ice:

| Stock solution | Final Concentration |
| --- | --- |
| 5 × DMEC | 1 × DMEM |
| 3 mg/ml vitrogen | 2 mg/ml |
| ddH2O | optimal |
| NHDF | 2 × 10~5 cells/ml |
| FBS | 1% |

4) Aspire 2% BSA from 24 well plate, add collagen-cell mixture 350 ul/well, and incubate the plate in 37° C. CO2 incubator.
  5) After 1 hr, add DMEM+5% FBS medium 0.5 ml/well, use a 10 ul tip Detach the collagen gel from the edge of each well, then incubate for 2 days. The fibroblast cells will contract the collagen gel Step 2: Prepare 3D Fibrin Wound Clot and Embed Wounded Collagen Culture
  1) Prepare fibrinogen solution (1 mg/ml) with or without testing regents. 350 ul fibrinogen solution for each well in eppendorf tube.

| Stock solution | Final Concentration |
| --- | --- |
| 5 × DMEC | 1 × DMEM |
| Fibrinogen | 1 mg/ml |
| ddH2O | optimal |
| testing regents | optimal concentration |
| FBS | 1% or 5% |

2) Cut each contracted collagen gel from middle with scissors. Wash the gel with PBS and transfer the gel to the center of each well of 24 well plate
  3) Add 1.5 ul of human thrombin (0.25 U/ul) to each tube, mix well and then add the solution around the collagen gel, the solution will polymerize in 10 mins.

After 20 mins, add DMEM+1% (or 5%) FBS with or without testing agent, 450 ul/well and incubate the plate in 37° C. CO2 incubator for up to 5 days. Take pictures on each day.

In Vivo Wound Healing in Diabetic Rats:
  Using an acute incision wound model in diabetic rats, the effects of Nicotine, nicotinic acid analogs and its conjugated forms are tested. The rate of wound closure, breaking strength analyses and histology are performed periodically on days 3-21.

In part, this invention provides compositions and methods for promoting angiogenesis in a subject in need thereof. Conditions amenable to treatment by promoting angiogenesis include, for example, occlusive peripheral vascular disease and coronary diseases, in particular, the occlusion of coronary vessels, and disorders associated with the occlusion of the peripheral vasculature and/or coronary blood vessels, erectile dysfunction, stroke, and wounds. Also disclosed are compositions and methods for promoting angiogenesis and/or recruiting collateral blood vessels in a patient in need thereof. The compositions include an effective amount of polymeric forms of Nicotine, nicotinic acid analogs and derivatives and an effective amount of an adenosine and/or nitric oxide donor. The compositions can be in the form of a sterile, injectable, pharmaceutical formulation that includes an effective amount of Nicotine, nicotinic acid analogs and adenosine derivatives in a physiologically and pharmaceutically acceptable carrier, optionally with one or more excipients.

A major reason for heart failure following acute myocardial infarction is an inadequate response of new blood vessel formation, i.e., angiogenesis. Nicotine, nicotinic acid analogs are beneficial in heart failure and stimulate coronary angiogenesis. The methods of the invention include, in part, delivering a single treatment of a Nicotine, nicotinic acid analogs at the time of infarction either by direct injection into the myocardium or by simulation of coronary injection by intermittent aortic ligation to produce transient isovolumic contractions to achieve angiogenesis and/or ventricular remodeling.

Accordingly, in one aspect the invention features methods for treating occlusive vascular disease, coronary disease, myocardial infarction, ischemia, stroke, and/or peripheral artery vascular disorders by promoting angiogenesis by administering to a subject in need thereof an amount of a polymeric form of Nicotine, nicotinic acid analogs, or an analog thereof, effective for promoting angiogenesis.

Examples of polymeric forms of Nicotine, nicotinic acid analogs, conjugated to polyvinyl alcohol, acrylic acid ethylene co-polymer or polylactic acid are provided herein.

The methods also involve the co-administration of Nicotine, nicotinic acid analogs and an effective amount of an adenosine and/or NO donor in low, daily dosages for a week or more. One or both components can be delivered locally via catheter. Nicotine, nicotinic acid analogs peptides, analogs, and derivatives in vivo can be delivered to capillary beds surrounding ischemic tissue by incorporation of the compounds in an appropriately sized liposome or microparticle. Nicotine, nicotinic acid analogs peptides, analogs, polymeric forms and derivatives can be targeted to ischemic tissue by covalent linkage with a suitable antibody.

The method may be used as a treatment to restore cardiac function after a myocardial infarction. The method may also be used to improve blood flow in patients with coronary artery disease suffering from myocardial ischemia or inadequate blood flow to areas other than the heart including, for example, occlusive peripheral vascular disease (also known as peripheral arterial occlusive disease), or erectile dysfunction.

Wound Healing

Wound angiogenesis is an important part of the proliferative phase of healing. Healing of any skin wound other than the most superficial cannot occur without angiogenesis. Not only does any damaged vasculature need to be repaired, but the increased local cell activity necessary for healing requires an increased supply of nutrients from the bloodstream. Moreover, the endothelial cells which form the lining of the blood vessels are important in themselves as organizers and regulators of healing.

Thus, angiogenesis provides a new microcirculation to support the healing wound. The new blood vessels become clinically visible within the wound space by four days after injury. Vascular endothelial cells, fibroblasts, and smooth muscle cells all proliferate in coordination to support wound granulation. Simultaneously, re-epithelialization occurs to reestablish the epithelial cover. Epithelial cells from the wound margin or from deep hair follicles migrate across the wound and establish themselves over the granulation tissue and provisional matrix. The role of topically applied Nicotine, nicotinic acid analogs or polymeric forms in wound healing therefore represents a novel strategy to accelerate wound healing in diabetics and in non-diabetics with impaired wound healing abilities. Topical administration can be in the form of attachment to a band-aid. Additionally, nano-polymers and nano-particles can be used as a matrix for local delivery of Nicotine, nicotinic acid analogs and its analogs. This will aid in time controlled delivery into the cellular and tissue target.

Accordingly, another embodiment of the invention features methods for treating wounds by promoting angiogenesis by administering to a subject in need thereof an amount of a polymeric form of Nicotine, nicotinic acid analogs, or an analog thereof, effective for promoting angiogenesis.

Methods of Treatment

Nicotine, nicotinic acid analogs, polymeric forms, and derivatives can be used in a method for promoting angiogenesis in a patient in need thereof. The method involves the co-administration of an effective amount of Nicotine, nicotinic acid analogs, polymeric forms, and derivatives in low, daily dosages for a week or more. The method may be used as a treatment to restore cardiac function after a myocardial infarction. The method may also be used to improve blood flow in patients with coronary artery disease suffering from myocardial ischemia or inadequate blood flow to areas other than the heart, for example, peripheral vascular disease, for example, peripheral arterial occlusive disease, where decreased blood flow is a problem.

The compounds can be administered via any medically acceptable means which is suitable for the compound to be administered, including oral, rectal, topical or parenteral (including subcutaneous, intramuscular and intravenous) administration. For example, adenosine has a very short half-life. For this reason, it is preferably administered intravenously. However, adenosine A.sub.2 agonists have been developed which have much longer half-lives, and which can be administered through other means. Nicotine, nicotinic acid analogs, polymeric forms, and derivatives can be administered, for example, intravenously, oral, topical, intranasal administration.

In some embodiments, the Nicotine, nicotinic acid analogs, polymeric forms, and derivatives are administered via different means.

The amounts of the Nicotine, nicotinic acid analogs peptides, its analogs, polymeric forms, and derivatives required to be effective in stimulating angiogenesis will, of course, vary with the individual being treated and is ultimately at the discretion of the physician. The factors to be considered include the condition of the patient being treated, the efficacy of the particular adenosine A.sub.2 receptor agonist being used, the nature of the formulation, and the patient's body weight. Occlusion-treating dosages of Nicotine, nicotinic acid analogs or its polymeric forms, and derivatives are any dosages that provide the desired effect.

Formulations

The compounds described above are preferably administered in a formulation including Nicotine, nicotinic acid analogs or its polymeric forms, and derivatives together with an acceptable carrier for the mode of administration. Any formulation or drug delivery system containing the active ingredients, which is suitable for the intended use, as are generally known to those of skill in the art, can be used. Suitable pharmaceutically acceptable carriers for oral, rectal, topical or parenteral (including subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

Formulations suitable for parenteral administration conveniently include sterile aqueous preparation of the active compound, which is preferably isotonic with the blood of the recipient. Thus, such formulations may conveniently contain distilled water, 5% dextrose in distilled water or saline. Useful formulations also include concentrated solutions or solids containing the compound of formula (I), which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

In one embodiment, the Nicotine, nicotinic acid analogs or its polymeric forms, and adenosine derivatives can be formulated into a liposome or microparticle, which is suitably sized to lodge in capillary beds following intravenous administration. When the liposome or microparticle is lodged in the capillary beds surrounding ischemic tissue, the agents can be administered locally to the site at which they can be most effective. Suitable liposomes for targeting ischemic tissue are generally less than about 200 nanometers and are also typically unilamellar vesicles, as disclosed, for example, in U.S. Pat. No. 5,593,688 to Baldeschweiler, entitled "Liposomal targeting of ischemic tissue," the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

The formulations may conveniently be presented in unit dosage form and may be prepared by any of the methods well known in the art of pharmacy. All methods include the step of bringing the active compound into association with a carrier, which constitutes one or more accessory ingredients. In general, the formulations are prepared by uniformly and intimately bringing the active compound into association with a liquid carrier or a finely divided solid carrier and then, if necessary, shaping the product into desired unit dosage form.

The formulations can optionally include additional components, such as various biologically active substances such as growth factors (including TGF-.beta., basic fibroblast growth factor (FGF2), epithelial growth factor (EGF), transforming growth factors alpha. and .beta. (TGF alpha. and beta.), nerve growth factor (NGF), platelet-derived growth factor (PDGF), and vascular endothelial growth factor/vascular permeability factor (VEGF/VPF), antiviral, antibacterial, anti-inflammatory, immuno-suppressant, analgesic, vascularizing agent, and cell adhesion molecule.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Materials & Methods

Reagents: All reagents were chemical grade and purchased from Sigma Chemical Co. (St. Louis, Mo.) or through VWR Scientific (Bridgeport, N.J.). Cortisone acetate, bovine serum albumin (BSA) and gelatin solution (2% type B from bovine skin) were purchased from Sigma Chemical Co. Fertilized chicken eggs were purchased from Charles River Laboratories, SPAFAS Avian Products & Services (North Franklin, Conn.).

Chorioallantoic membrane (CAM) Model of Angiogenesis: In vivo Neovascularization was examined by methods described previously. 9-12 Ten-day-old chick embryos were purchased from SPAFAS (Preston, Conn.) and incubated at 37° C. with 55% relative humidity. A hypodermic needle was used to make a small hole in the shell concealing the air sac, and a second hole was made on the broad side of the egg, directly over an avascular portion of the embryonic membrane that was identified by candling. A false air sac was created beneath the second hole by the application of negative pressure at the first hole, causing the CAM to separate from the shell. A window approximately 1.0 cm 2 was cut in the shell over the dropped CAM with a small-crafts grinding wheel (Dremel, division of Emerson Electric Co.), allowing direct access to the underlying CAM. FGF2 (1 µg/mL) was used as a standard proangiogenic agent to induce new blood vessel branches on the CAM of 10-day-old embryos. Sterile disks of No. 1 filter paper (Whatman International) were pretreated with 3 mg/mL cortisone acetate. Nicotine, nicotinic acid analogs, FGF2 or control solvents, and inhibitors were then applied to the disks and the disks allowed to dry. The disks were then suspended in PBS and placed on growing CAMs. Filters treated were placed on the first day of the 3-day incubation, with antibody to FGF2 added 30 minutes later to selected samples as indicated. At 24 hours, the MAPK cascade inhibitor PD 98059 was also added to CAMs topically by means of the filter disks.

Microscopic Analysis of CAM Sections: After incubation at 37° C. with 55% relative humidity for 3 days, the CAM tissue directly beneath each filter disk was resected from control and treated CAM samples. Tissues were washed 3× with PBS, placed in 35-mm Petri dishes (Nalge Nunc), and examined under an SV6 stereomicroscope (Zeiss) at ×50 magnification. Digital images of CAM sections exposed to filters were collected using a 3-charge-coupled device color video camera system (Toshiba) and analyzed with Image-Pro software (Media Cybernetics). The number of vessel branch points contained in a circular region equal to the area of each filter disk were counted. One image was counted in each CAM preparation, and findings from 8 to 10 CAM preparations were analyzed for each treatment condition (Nicotine, nicotinic acid analogs). The resulting angiogenesis index is the mean±SEM of new branch points in each set.

Nicotine, Nicotinic Acid Analogs Delivery

There are two delivery approaches. In the first, Nicotine, nicotinic acid analogs is directly injected into the peri-infarct myocardium. As the demarcation between normal and ischemic myocardium is easily identified during the acute open chest occlusion, this approach provides sufficient delivery of hormone to detect angiogenic effects.

Although the first model is useful in patients undergoing coronary artery bypass surgery, and constitutes proof of principle that one local injection induces angiogenesis, a broader approach using a second model can also be used. In the second model, a catheter retrograde is placed into the left ventricle via a carotid artery in the anesthetized rat prior to inducing myocardial infarction. Alternatively, a direct needle puncture of the aorta, just above the aortic valve, is performed. The intracoronary injection of the Nicotine, nicotinic acid analogs is then simulated by abruptly occluding the aorta above the origin of the coronary vessels for several seconds, thereby producing isovolumic contractions. Nicotine, nicotinic acid analogs is then injected into the left ventricle or aorta immediately after aortic constriction. The resulting isovolumic contractions propel blood down the coronary vessels perfusing the entire myocardium with Nicotine, nicotinic acid analogs. This procedure can be done as many times as necessary to achieve effectiveness. The number of injections depends on the doses used and the formation of new blood vessels.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

Compositions and methods for treatment of occlusive peripheral vascular disease and coronary diseases, in particular, the occlusion of coronary vessels, and disorders associated with the occlusion of the peripheral vasculature and/or coronary blood vessels are disclosed. Also disclosed are compositions and methods for promoting angiogenesis and/or recruiting collateral blood vessels in a patient in need thereof. The compositions include an effective amount of Nicotinic acid or nicotine, polymeric forms, and derivatives. The methods involve the co-administration of an effective amount of Nicotinic acid or nicotine, polymeric forms, and derivatives in low, daily dosages for a week or more.

This invention provides novel compositions and methods for treatment of occlusive peripheral vascular disease and coronary diseases, in particular, the occlusion of coronary vessels, and disorders associated with the occlusion of the peripheral vasculature and/or coronary blood vessels, are disclosed. Also disclosed are compositions and methods for promoting angiogenesis and/or recruiting collateral blood vessels in a patient in need thereof. The compositions include an effective amount of polymeric forms of Nicotinic acid, analogs and derivatives, with an effective amount of an adenosine and/or nitric oxide donor o other vasodilators. The compositions can be in the form of a sterile, injectable, pharmaceutical formulation that includes an angiogenically effective amount of Nicotine, nicotinic acid, polymeric forms or their combinations and adenosine derivatives in a physiologically and pharmaceutically acceptable carrier, optionally with one or more excipients. The methods involve the co-administration of an effective amount of Nicotine, nicotinic acid, polymeric forms or their combinations and an effective amount of an apomorphine, adenosine and/or NO donor in low, daily dosages for a week or more. One or both components can be delivered locally via catheter. Nicotine, nicotinic acid, polymeric forms or their combinations can be delivered to capillary beds surrounding ischemic tissue by incorporation of the compounds in an appropriately sized liposome or microparticle. Nicotine, nicotinic acid, polymeric forms or their combinations can be targeted to ischemic tissue by covalent linkage with a suitable antibody.

The method may be used as a treatment to restore cardiac function after a myocardial infarction. The method may also be used to improve blood flow in patients with coronary artery disease suffering from myocardial ischemia or inadequate blood flow to areas other than the heart, for example, occlusive peripheral vascular disease (also known as peripheral arterial occlusive disease), where decreased blood flow is a problem.

What is claimed is:

1. A pharmaceutical composition, said composition comprising:
   nicotine and
   a nicotinic acid analog, wherein the nicotinic acid analog is conjugated to a member selected from the group consisting of acrylic acid ethylene co-polymer, polyethyleneglycol (PEG), and polylactic acid and wherein the nicotine and the nicotinic acid analog in the composition are in an amount effective for promoting angiogenesis in a subject as a result of administering the composition to the subject.

2. The composition of claim 1, wherein the nicotinic acid analog is conjugated to the member via a covalent bond.

3. The composition of claim 2, wherein the covalent bond is an ester linkage or an anhydride linkage.

4. The composition of claim 1, wherein the nicotinic acid analog is encapsulated or incorporated in a microparticle or liposome.

5. The composition of claim 4, wherein the microparticle or liposome has a size less than 200 nanometers.

6. The composition of claim 1, wherein the composition further comprises at least one substance selected from the group consisting of a growth factor, a vasodilator, an anticoagulant, and combinations thereof.

7. The composition of claim 6, wherein the at least one substance comprises the growth factor.

8. The composition of claim 7, wherein the growth factor is a fibroblast growth factor (FGF2) or a vascular endothelial growth factor (VEGF).

9. The composition of claim 6, wherein the at least one substance comprises the vasodilator.

10. The composition of claim 9, wherein the vasodilator is selected from the group consisting of nitric oxide donors, adenosine analogs, phosphodiaesterase inhibitors, and apomorphme.

11. The composition of claim 6, wherein the at least one substance comprises the anticoagulant.

12. The composition of claim 11, wherein the anticoagulant is selected from the group consisting of heparin, heparin derivatives, anti-factor Xa, anti-thrombin, aspirin, clopidgrel, and combinations thereof.

13. The composition of claim 6, wherein the at least one substance comprises the growth factor and the vasodilator.

14. The composition of claim 6, wherein the at least one substance comprises the growth factor and the anticoagulant.

15. The composition of claim 6, wherein the at least one substance comprises the vasodilator and the anticoagulant.

16. The composition of claim 6, wherein the at least one substance comprises the growth factor, the vasodilator, and the anticoagulant.

* * * * *